United States Patent
Schulze zur Wiesche et al.

(10) Patent No.: US 6,790,240 B2
(45) Date of Patent: Sep. 14, 2004

(54) SOLID COLORANT FOR KERATIN FIBERS

(75) Inventors: Erik Schulze zur Wiesche, Hamburg (DE); Britta Bossmann, Erkrath (DE); Detlef Hollenberg, Erkrath (DE); Michael Dreja, Cologne (DE)

(73) Assignee: Henkel Kommanditgesellschaft aug Aktien, Duesseldorf (DE)

(*) Notice: Subject to any disclaimer, the term of this patent is extended or adjusted under 35 U.S.C. 154(b) by 0 days.

(21) Appl. No.: 10/172,295

(22) Filed: Jun. 14, 2002

(65) Prior Publication Data

US 2003/0172469 A1 Sep. 18, 2003

Related U.S. Application Data

(63) Continuation of application No. PCT/EP00/12805, filed on Dec. 15, 2000.

(30) Foreign Application Priority Data

Dec. 20, 1999 (DE) .......................................... 199 61 910

(51) Int. Cl.$^7$ ................................................. A61K 7/13
(52) U.S. Cl. ........................ 8/405; 8/406; 8/409; 8/450; 8/519
(58) Field of Search ............................ 8/405, 406, 409, 8/450, 519

(56) References Cited

U.S. PATENT DOCUMENTS

| | | | | |
|---|---|---|---|---|
| 3,849,064 A | * | 11/1974 | Wiskott ........................ 8/10.2 |
| 3,861,868 A | * | 1/1975 | Milbrada ....................... 8/10.2 |
| 4,003,699 A | | 1/1977 | Rose et al. .................... 8/10.2 |
| 4,865,774 A | | 9/1989 | Fabry et al. ................ 252/554 |
| 4,931,218 A | | 6/1990 | Schenker et al. ........... 252/551 |
| 5,061,289 A | | 10/1991 | Clausen et al. ................. 8/405 |
| 5,205,837 A | | 4/1993 | Andrean et al. ............... 8/405 |
| 5,294,726 A | | 3/1994 | Behler et al. ................. 554/98 |
| 5,380,340 A | | 1/1995 | Neunhoeffer et al. .......... 8/409 |
| 5,534,267 A | | 7/1996 | Neunhoeffer et al. ....... 424/701 |
| 5,663,366 A | | 9/1997 | Neunhoeffer et al. .... 548/371.4 |
| 5,766,576 A | | 6/1998 | Löwe et al. ................... 424/62 |
| 5,769,903 A | * | 6/1998 | Audousset et al. ............ 8/405 |
| 6,099,592 A | | 8/2000 | Vidal et al. .................... 8/409 |
| 6,284,003 B1 | | 9/2001 | Rose et al. .................... 8/412 |

FOREIGN PATENT DOCUMENTS

| | | |
|---|---|---|
| DE | 11 178 26 | 11/1961 |
| DE | 2 215 303 | 10/1972 |
| DE | 23 59 399 | 6/1975 |
| DE | 37 23 354 | 1/1989 |
| DE | 37 25 030 | 2/1989 |
| DE | 38 43 892 | 6/1990 |
| DE | 39 26 344 | 2/1991 |
| DE | 41 33 957 | 4/1993 |
| DE | 42 33 874 | 5/1996 |
| DE | 195 43 988 | 5/1997 |
| EP | 0 273 005 | 6/1988 |
| EP | 0 467 767 | 9/1994 |
| EP | 0 530 229 | 6/1995 |
| EP | 0 740 931 | 8/1997 |
| FR | 1 101 092 | 9/1955 |
| GB | 524 293 | 8/1940 |
| GB | 749 045 | 5/1956 |
| GB | 878098 | 9/1961 |
| GB | 1 026 978 | 4/1966 |
| GB | 1 153 196 | 5/1969 |
| GB | 2 187 456 | 9/1987 |
| JP | 46 004280 | 2/1971 |
| JP | 02 019576 | 1/1990 |
| WO | WO 91/17739 | 11/1991 |
| WO | WO 94/08969 | 4/1994 |
| WO | WO 94/08970 | 4/1994 |
| WO | WO 96/15765 | 5/1996 |
| WO | WO 99/09958 | 3/1999 |
| WO | WO 01/45647 | 6/2001 |
| WO | WO 01/45654 | 6/2001 |
| WO | WO 01/45655 | 6/2001 |

OTHER PUBLICATIONS

Derwent Abstract of JP 46 004280, AN 1971–09180s, XP002161614, week 197105, Derwent Publications Ltd, London (1971).
The Science of Hair Care, Chapter 7, pp. 235–261, published in vol. 7 of Dermatology, Marcel Dekker Inc. NY/Basle (1986).
The Science of Hair Care, Chapter 8, pp. 263–286, published in vol. 7 of Dermatology, Marcel Dekker Inc. NY/Basle (1986).
EU Inventory of Cosmetic Ingredients, Colipa, Mar. 1996 on diskette.
Falbe, et al., "Römpp Chemie Lexikon," $9^{th}$ Edition, vol. 6, p. 4440, Verlag Stuttgart, New York, (1992).
Voigt, "Lehrbuch der pharmazeutischen Technologie," $6^{th}$ Edition, pp. 182–184 (1987).
K. Schrader, "Grundlagen un Rezepturen der Kosmetika [Bases and Formulations in Cosmetics]," $2^{nd}$ Edition, pp. 782–799, Huethig Buch Verlag, Heidelberg, Germany (1998).
"Determination of the water vapour transmission rate of plastic film, rubber sheeting, paper, board and other sheet materials by gravimetry," DIN 53 122–1 pp. 1–7, DIN Deutches Institut Für Normung e.V., Berlin, Germany, (Aug. 2001).
"Standard Test Methods for Water Vapor Transmission of Materials," ASTM E–96–53T, Annual Book of ASTM Standards, vol. 14.02, pp. 1–8, ASTM International, (2000).
Hans Domininghaus, Die Kunststoffe und ihre Eigneschaften, $3^{rd}$ Edition, p. 193, VDI Verlag, (1998).

* cited by examiner

Primary Examiner—Mark Kopec
Assistant Examiner—Eisa Elhilo
(74) Attorney, Agent, or Firm—Stephen D. Harper; Gregory M. Hill

(57) ABSTRACT

A shaped body is provided for preparing coloring compositions and for coloring keratin fibers. The shaped body contains at least one dye precursor, at least one oxidizing agent, and at least one alkalinizing agent. The shaped body is placed in a composition containing water to form a coloring composition that can be applied to keratin fibers.

21 Claims, No Drawings

SOLID COLORANT FOR KERATIN FIBERS

CROSS-REFERENCE TO RELATED APPLICATIONS

This application is a continuation under 35 U.S.C. §365 (c) and 35 U.S.C. §120 of international application PCT/EP00/12805, filed on Dec. 15, 2000, the international application not being published in English. This application also claims priority under 35 U.S.C. §119 to DE 199 61 910.7, filed on Dec. 20, 1999.

BACKGROUND OF THE INVENTION

The present invention relates to shaped bodies for coloring keratin fibers, which, in addition to dye precursors and oxidizing agents, additionally comprise an alkalinizing agent, to the use of these compositions for the preparation of hair-coloring preparations, and to a method of coloring keratin fibers using these shaped bodies.

Human hair is nowadays treated in many diverse ways with hair cosmetic preparations. These include, for example, cleansing of the hair using shampoos, care and regeneration using rinses and cures, and bleaching, coloring and shaping the hair using colorants, tints, waving compositions and styling preparations. In this connection, compositions for changing or shading the color of the hair on the head play a prominent role.

For temporary colorations, use is usually made of colorants or tints which comprise substantive dyes as coloring component. These are dye molecules which attach directly to the hair and do not require an oxidative process to develop the color. These dyes include, for example, henna, which has been known from antiquity for coloring body and hair. These colorations are generally significantly more sensitive toward shampooing than the oxidative colorations, meaning that an often undesired shift in shade or even a visible "decoloration" occurs very much more quickly.

For permanent intensive colorations with corresponding fastness properties, use is made of oxidation dyes. Such dyes usually comprise oxidation dye precursors, termed developer components and coupler components. The developer components form, under the influence of oxidizing agents or of atmospheric oxygen among themselves, or with coupling with one or more coupler components, the actual dyes. The oxidation dyes are characterized by excellent, long-lasting color results. For natural colorations, it is usually necessary to use a mixture of a relatively large number of oxidation dye precursors; in many cases, substantive dyes are also used for shading.

Finally, a novel coloring process has recently attracted significant attention. In this process, precursors of the natural hair dye melanin are applied to the hair; these then develop nature-analogous dyes within the scope of oxidative processes within the hair. Such a process using 5,6-dihydroxyindoline as dye precursor has been described in EP-B1-530 229. The application, in particular repeated application, of compositions comprising 5,6-dihydroxyindoline enables people with gray hair to regain their natural hair color. The coloration can be developed here with atmospheric oxygen as the sole oxidizing agent, meaning that recourse does not have to be made to further oxidizing agents. In people with originally mid-blond to brown hair, the indoline can be used as the sole dye precursor. For application in the case of people with an originally red and, in particular, dark to black hair color, satisfactory results can, by contrast, often only be achieved through the co-use of further dye components, in particular specific oxidation dye precursors.

Hair colorants are usually formulated in the form of aqueous emulsions or color gels which, where appropriate, are mixed with an oxidizing agent preparation directly prior to application. However, this process could still be improved upon with regard to the storage stability of the formulations, the dosability and ease of handling.

JP-B-46-004280 has proposed the formulation of hair colorants in the form of a tablet, where the color preparation comprising the dye, and the oxidizing agent preparation are not in contact. It has been proposed that the hair coloring components and the oxidizing agent preparation be separated by an inert interlayer, for example made of Avicel, starch or cellulose derivatives. Tablets are usually to be heavily compressed in order to prevent them from breaking apart or being heavily abraded during preparation, storage and transportation. However, the color result which can be achieved with these shaped bodies is still inferior to the color performance of conventional two-component systems, and this form of formulation has hitherto not successfully penetrated the market.

The object was therefore to optimize the color shaped bodies with regard to their coloring properties and their dissolution behavior.

Surprisingly, it has now been found that, by using an additional alkalinizing agent, the colorations which can be achieved can be significantly improved with regard to their intensity and fastness properties, and the shaped bodies are characterized by a significantly reduced dissolution time.

SUMMARY OF THE INVENTION

The present invention firstly therefore provides shaped bodies for coloring keratin fibers, which comprise, in a cosmetically acceptable carrier, at least one dye precursor, at least one oxidizing agent and additionally at least one alkalinizing agent.

DETAILED DESCRIPTION OF THE INVENTION

Keratin fibers are to be understood according to the invention as meaning furs, wool, feathers and, in particular, human hair. Although the shaped bodies according to the invention are primarily suitable for coloring keratin fibers, nothing in principle opposes a use in other fields.

Alkalinizing Agents

In principle, the alkalinizing agents are not subject to any limitations. Suitable alkalinizing agents are, for example, ammonium salts; carbonates, amino acids, alkali metal hydroxides or alkaline earth metal hydroxides and organic amines.

In a preferred embodiment of the present invention, solid alkalinizing agents are used.

In a further embodiment of the present invention, it may be preferred to use alkalinizing agents characterized by good solubility in water. According to the invention, readily water-soluble compounds are compounds of which at least 5 g dissolve in 100 ml of water at 15° C. Particular preference is given to compounds with a solubility in water of more than 7.5 g in 100 ml of water at 15° C.

In addition, the alkalinizing agents which develop only a slight partial pressure outside of the shaped body following their incorporation into the shaped bodies according to the invention have proven particularly preferred.

In a preferred embodiment of the present invention, the alkalinizing agents used are amino acids or oligopeptides with at least one amino group and a carboxyl or a sulfo group whose 2.5% strength aqueous solution has a pH of greater than 9.0.

Within the scope of this embodiment, aminocarboxylic acids are particularly preferred, in particular α-aminocarboxylic acids and ω-aminocarboxylic acids. Of the α-aminocarboxylic acids, particular preference is given in turn to lysine and, in particular, to arginine.

The amino acids can be added to the shaped bodies according to the invention preferably in free form. In a number of cases, however, it is also possible to use the amino acids in salt form. Preferred salts are then the compounds with hydrohalic acids, in particular the hydrochlorides and the hydrobromides.

Furthermore, the amino acids can also be used in the form of oligopeptides and protein hydrolysates, if it is ensured that the required amounts of the amino acids used according to the invention are present therein. In this connection, reference is made to the disclosure of DE-A 22 15 303, to which reference is expressly made.

A very particularly preferred alkalinizing agent is arginine, in particular in free form, but also used as hydrochloride since, in addition to its alkaline properties, it also significantly increases the penetration ability of the dyes.

The alkalinizing agent is present in the shaped bodies according to the invention preferably in amounts of from 0.5 to 20% by weight, in particular from 5 to 15% by weight, based on the total composition.

Oxidizing Agents

Although the choice of oxidizing agent is in principle not subject to any limitations, it may be preferred according to the invention to use addition products of hydrogen peroxide, in particular onto urea, melamine or sodium borate, as oxidizing agents. The use of percarbamide is particularly preferred.

In addition, it is possible to carry out the oxidation using enzymes, the enzymes being used both for generating oxidizing percompounds, and also for enhancing the effect of a small amount of oxidizing agents present.

Thus, the enzymes (enzyme class 1: oxidoreductases) can transfer electrons from suitable developer components (reducing agents) to atmospheric oxygen. Preference is given here to oxidases, such as tyrosinase and laccase, but also glucose oxidase, uricase or pyruvate oxidase. Furthermore, mention may be made of the action to enhance the effect of small amounts (e.g. 1% and less, based on the overall composition) of hydrogen peroxide by peroxidases.

The development of the color can also be aided and increased by adding certain metal ions to the shaped body. Such metal ions are, for example, $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$ and $Al^{3+}$. Here, $Zn^{2+}$, $Cu^{2+}$ and $Mn^{2+}$ are particularly suitable. The metal ions can, in principle, be used in the form of any desired physiologically compatible salt. Preferred salts are the acetates, sulfates, halides, lactates and tartrates. By using these metal salts, it is possible both to accelerate the development of the coloration, and also to influence the color shade in a targeted manner. It has, however, also proven practicable to use the metal ions in the form of their complexes or else positioned on zeolites to increase the coloring power.

Dye Precursors

The present invention is not subject to any limitations with regard to the dye precursors used in the shaped bodies according to the invention. The shaped bodies according to the invention can comprise, as dye precursors, oxidation dye precursors of the developer and coupler type, and precursors of nature-analogous dyes, such as indole and indoline derivatives, and mixtures of representatives of these groups.

The developer components usually used are primary aromatic amines with a further free or substituted hydroxyl or amino group situated in the para or ortho position, diaminopyridine derivatives, heterocyclic hydrazones, 4-aminopyrazole derivatives, and 2,4,5,6-tetraaminopyrimidine and derivatives thereof.

It may be preferred according to the invention to use a p-phenylenediamine derivative or one of its physiologically compatible salts as developer component. Particular preference is given to p-phenylenediamine derivatives of the formula (E1)

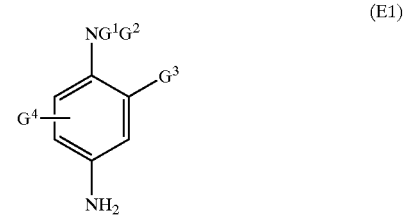

(E1)

where $G^1$ is a hydrogen atom, a $C_1$- to $C_4$-alkyl radical, a $C_1$- to $C_4$-monohydroxyalkyl radical, a $C_2$- to $C_4$-polyhydroxyalkyl radical, a ($C_1$- to $C_4$)-alkoxy-($C_1$- to $C_4$)-alkyl radical, a 4'-aminophenyl radical or a $C_1$- to $C_4$-alkyl radical which is substituted by a nitrogen-containing group, a phenyl radical or a 4'-aminophenyl radical;

$G^2$ is a hydrogen atom, a $C_1$- to $C_4$-alkyl radical, a $C_1$- to $C_4$-monohydroxyalkyl radical, a $C_2$- to $C_4$-polyhydroxyalkyl radical, a ($C_1$- to $C_4$)-alkoxy-($C_1$- to $C_4$)-alkyl radical or a $C_1$- to $C_4$-alkyl radical which is substituted by a nitrogen-containing group;

$G^3$ is a hydrogen atom, a halogen atom, such as a chlorine, bromine, iodine or fluorine atom, a $C_1$- to $C_4$-alkyl radical, a $C_1$- to $C_4$-monohydroxyalkyl radical, a $C_1$- to $C_4$-hydroxyalkoxy radical, a $C_1$- to $C_4$-acetylaminoalkoxy radical, a $C_1$- to $C_4$-mesylaminoalkoxy radical or a $C_1$- to $C_4$-carbamoylaminoalkoxy radical;

$G^4$ is a hydrogen atom, a halogen atom or a $C_1$- to $C_4$-alkyl radical or if $G^3$ and $G^4$ are in the ortho position relative to one another, they can together form a bridging α,ω-alkylenedioxo group, such as, for example, an ethylenedioxy group.

Examples of the $C_1$- to $C_4$-alkyl radicals named as substituents in the compounds according to the invention are the groups methyl, ethyl, propyl, isopropyl and butyl. Ethyl and methyl are preferred alkyl radicals. $C_1$- to $C_4$-alkoxy radicals preferred according to the invention are, for example, a methoxy or an ethoxy group. In addition, preferred examples of a $C_1$- to $C_4$-hydroxyalkyl group which may be mentioned are a hydroxymethyl group, a 2-hydroxyethyl group, a 3-hydroxypropyl group or a 4-hydroxybutyl group. A 2-hydroxyethyl group is particularly preferred. Examples of halogen atoms according to the invention are F, Cl or Br atoms, Cl atoms being very particularly preferred. The other terms used are derived, according to the invention, from the definitions given here. Examples of nitrogen-containing groups of the formula (II) are, in particular, the amino groups, $C_1$- to $C_4$-monoalkylamino groups, $C_1$- to $C_4$-dialkylamino groups, $C_1$- to $C_4$-trialkylammonium groups, $C_1$- to $C_4$-monohydroxyalkylamino groups, imidazolinium and ammonium.

Particularly preferred p-phenylenediamines of the formula (E1) are chosen from p-phenylenediamine, p-tolylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)-aniline, N,N-bis(β-hydroxyethyl)-p-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl,β-hydroxyethyl)-p-phenylenediamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-(β-acetylaminoethyloxy)-p-phenylenediamine, N-(β-methoxyethyl)-p-phenylenediamine and 5,8-diaminobenzo-1,4-dioxane and their physiologically compatible salts.

According to the invention, very particularly preferred p-phenylenediamine derivatives of the formula (E1) are p-phenylenediamine, p-tolylenediamine, 2-(β-hydroxyethyl)-p-phenylenediamine and N,N-bis(β-hydroxyethyl)-p-phenylenediamine.

According to the invention, it may also be preferred to use compounds which contain at least two aromatic nuclei which are substituted by amino and/or hydroxyl groups, as developer component.

Of the binuclear developer components which can be used in the coloring compositions according to the invention, particular mention may be made of the compounds which conform to the following formula (E2), and of their physiologically compatible salts:

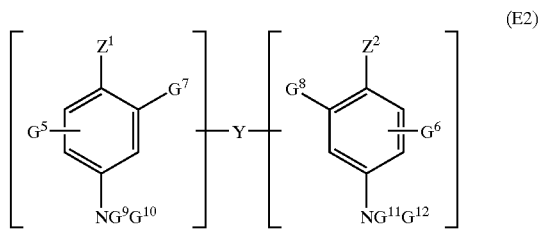

(E2)

where:
- $Z^1$ and $Z^2$, independently of one another, are a hydroxyl or $NH_2$ radical which may be substituted by a $C_1$- to $C_4$-alkyl radical, by a $C_1$- to $C_4$-hydroxyalkyl radical and/or by a bridging Y, or which may be part of a bridging ring system,
- the bridging Y is an alkylene group having 1 to 14 carbon atoms, such as, for example, a linear or branched alkylene chain or an alkylene ring which may be interrupted or ended by one or more nitrogen-containing groups and/or one or more heteroatoms, such as oxygen, sulfur or nitrogen atoms, and may possibly be substituted by one or more hydroxyl or $C_1$- to $C_8$-alkoxy radicals, or a direct bond,
- $G^5$ and $G^6$, independently of one another, are a hydrogen or halogen atom, a $C_1$- to $C_4$-alkyl radical, a $C_1$- to $C_4$-monohydroxyalkyl radical, a $C_2$- to $C_4$-polyhydroxyalkyl radical, a $C_1$- to $C_4$-aminoalkyl radical or a direct bond to the bridging Y,
- $G^7$, $G^8$, $G^9$, $G^{10}$, $G^{11}$ and $G^{12}$, independently of one another, are a hydrogen atom, a direct bond to the bridging Y or a $C_1$- to $C_4$-alkyl radical, with the provisos that
  the compounds of the formula (E2) contain only one bridging Y per molecule and
  the compounds of the formula (E2) contain at least one amino group which carries at least one hydrogen atom.

According to the invention, the substituents used in formula (E2) are defined analogously to the above statements.

Preferred binuclear developer components of the formula (E2) are, in particular: N,N'-bis(β-hydroxyethyl)-N,N'-bis(4'-aminophenyl)-1,3-diaminopropan-2-ol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, bis(2-hydroxy-5-aminophenyl)methane, 1,4-bis(4'-aminophenyl)diazacycloheptane, N,N'-bis(2-hydroxy-5-aminobenzyl)piperazine, N-(4'-aminophenyl)-p-phenylenediamine and 1,10-bis-(2',5'-diaminophenyl)-1,4,7,10-tetraoxadecane and their physiologically compatible salts.

Very particularly preferred binuclear developer components of the formula (E2) are N,N'-bis(β-hydroxyethyl)-N,N'-bis(4'-aminophenyl)-1,3-diaminopropan-2-ol, bis(2-hydroxy-5-aminophenyl)methane, N,N'-bis(4'-aminophenyl)-1,4-diazacycloheptane and 1,10-bis(2',5'-diaminophenyl)-1,4,7,10-tetraoxadecane or one of their physiologically compatible salts.

Furthermore, according to the invention it may be preferred to use a p-aminophenol derivative or one of its physiologically compatible salts as developer component. Particular preference is given to p-aminophenol derivatives of the formula (E3)

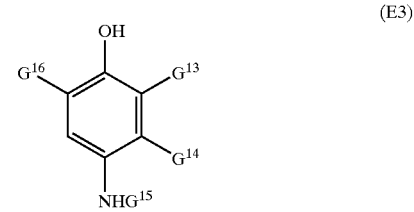

(E3)

where:
- $G^{13}$ is a hydrogen atom, a halogen atom, a $C_1$- to $C_4$-alkyl radical, a $C_1$- to $C_4$-monohydroxyalkyl radical, a ($C_1$- to $C_4$)-alkoxy-($C_1$- to $C_4$)-alkyl radical, a $C_1$- to $C_4$-aminoalkyl radical, a hydroxy-($C_1$- to $C_4$)-alkylamino radical, a $C_1$- to $C_4$-hydroxyalkoxy radical, a $C_1$- to $C_4$-hydroxyalkyl-($C_1$- to $C_4$)-aminoalkyl radical or a (di-$C_1$- to $C_4$-alkylamino)-($C_1$- to $C_4$)-alkyl radical, and
- $G^{14}$ is a hydrogen or halogen atom, a $C_1$- to $C_4$-alkyl radical, a $C_1$- to $C_4$-monohydroxyalkyl radical, a $C_2$- to $C_4$-polyhydroxyalkyl radical, a ($C_1$- to $C_4$)-alkoxy-($C_1$- to $C_4$)-alkyl radical, a $C_1$-to $C_4$-aminoalkyl radical or a $C_1$- to $C_4$-cyanoalkyl radical,
- $G^{15}$ is hydrogen, a $C_1$- to $C_4$-alkyl radical, a $C_1$- to $C_4$-monohydroxyalkyl radical, a $C_2$- to $C_4$-polyhydroxyalkyl radical, a phenyl radical or a benzyl radical, and
- $G^{16}$ is hydrogen or a halogen atom.

The substituents used in formula (E3) are defined according to the invention analogously to the above statements.

Preferred p-aminophenols of the formula (E3) are, in particular, p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(2-hydroxyethoxy) phenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol, 4-amino-2-fluorophenol, 4-amino-2-chlorophenol, 2,6-dichloro-4-aminophenol, 4-amino-2-((diethylamino)-methyl)phenol and their physiologically compatible salts.

Very particularly preferred compounds of the formula (E3) are p-aminophenol, 4-amino-3-methylphenol, 4-amino-2-aminomethylphenol and 4-amino-2-((diethylamino)methyl)phenol.

In addition, the developer component can be chosen from o-aminophenol and its derivatives, such as, for example, 2-amino-4-methylphenol or 2-amino-4-chlorophenol.

In addition, the developer component can be chosen from heterocyclic developer components, such as, for example, the pyridine, pyrimidine, pyrazole, pyrazole-pyrimidine derivatives and their physiologically compatible salts.

Preferred pyridine derivatives are, in particular, the compounds which are described in the patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine.

Preferred pyrimidine derivatives are, in particular, the compounds which are described in German patent DE 2 359 399, Japanese laid-open specification JP 02019576 A2 or in laid-open specification WO 96/15765, such as 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine.

Preferred pyrazole derivatives are, in particular, the compounds which are described in the patents DE 3 843 892, DE 4 133 957 and patent applications WO 94/08969, WO 94/08970, EP-740931 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4(β-hydroxyethyl)amino-1-methylpyrazole.

Preferred pyrazole-pyrimidine derivatives are, in particular, the derivatives of pyrazole-[1,5-a]-pyrimidine of the following formula (E4) and its tautomeric forms provided a tautomeric equilibrium exists:

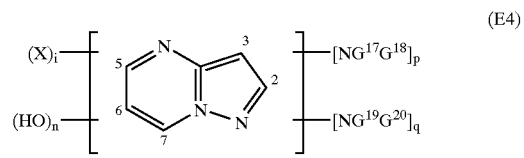

where:
G$^{17}$, G$^{18}$, G$^{19}$ and G$^{20}$, independently of one another, are a hydrogen atom, a C$_1$- to C$_4$-alkyl radical, an aryl radical, a C$_1$- to C$_4$-hydroxyalkyl radical, a C$_2$- to C$_4$-polyhydroxyalkyl radical, a (C$_1$- to C$_4$)-alkoxy-(C$_1$- to C$_4$)-alkyl radical, a C$_1$- to C$_4$-aminoalkyl radical, which may optionally be protected by an acetyl-ureide or sulfonyl radical, a (C$_1$- to C$_4$)-alkylamino-(C$_1$- to C$_4$)-alkyl radical, a di[(C$_1$- to C$_4$)-alkyl]-(C$_1$- to C$_4$)-aminoalkyl radical, where the dialkyl radicals optionally form a carbon cycle or a heterocycle with 5 or 6 chain members, a C$_1$- to C$_4$-hydroxyalkyl or a di(C$_1$- to C$_4$)-[hydroxyalkyl]-(C$_1$- to C$_4$)-aminoalkyl radical, the X radicals, independently of one another, are a hydrogen atom, a C$_1$- to C$_4$-alkyl radical, an aryl radical, a C$_1$- to C$_4$-hydroxyalkyl radical, a C$_2$- to C$_4$-polyhydroxyalkyl radical, a C$_1$- to C$_4$-aminoalkyl radical, a (C$_1$- to C$_4$)-alkylamino-(C$_1$- to C$_4$)-alkyl radical, a di[(C$_1$- to C$_4$)alkyl]-(C$_1$- to C$_4$)-aminoalkyl radical, where the dialkyl radicals optionally form a carbon cycle or a heterocycle with 5 or 6 chain members, a C$_1$- to C$_4$-hydroxyalkyl or a di(C$_1$- to C$_4$-hydroxyalkyl)aminoalkyl radical, an amino radical, a C$_1$- to C$_4$-alkyl or a di(C$_1$- to C$_4$-hydroxyalkyl)amino radical, a halogen atom, a carboxylic acid group or a sulfonic acid group, i has the value 0, 1, 2 or 3, p has the value 0 or 1, q has the value 0 or 1 and n has the value 0 or 1, with the proviso that the sum p+q is not 0, if p+q is 2, n has the value 0, and the groups NG$^{17}$G$^{18}$ and NG$^{19}$G$^{20}$ occupy the positions (2,3); (5,6); (6,7); (3,5) or (3,7);

if p+q is 1, n has the value 1, and the groups NG$^{17}$G$^{18}$ (or NG$^{19}$G$^{20}$) and the group OH occupy the positions (2,3); (5,6); (6,7); (3,5) or (3,7);

The substituents used in formula (E4) are defined according to the invention analogously to the above statements.

If the pyrazole-[1,5-a]-pyrimidine of the above formula (E4) contains a hydroxyl group on one of the positions 2, 5 or 7 of the ring system, a tautomeric equilibrium exists, which is shown, for example, in the following scheme:

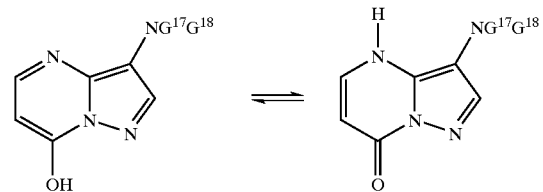

Of the pyrazole-[1,5-a]-pyrimidines of the above formula (E4), particular mention may be made of:

pyrazole-[1,5-a]-pyrimidine-3,7-diamine;

2,5-dimethylpyrazole-[1,5-a]-pyrimidine-3,7-diamine;
pyrazole(1,5-a]-pyrimidine-3,5-diamine;
2,7-dimethylpyrazole-[1,5-a]-pyrimidine-3,5-diamine;
3-aminopyrazole-[1,5-a]-pyrimidin-7-ol;
3-aminopyrazole-[1,5-a]-pyrimidin-5-ol;
2-(3-aminopyrazole-[1,5-a]-pyrimidin-7-ylamino) ethanol;
2-(7-aminopyrazole-[1,5-a]-pyrimidin-3-ylamino) ethanol;
2-[(3-aminopyrazole-[1,5-a]-pyrimidin-7-yl)-(2-hydroxyethyl)amino]ethanol;
2-[(7-aminopyrazole-[1,5-a]-pyrimidin-3-yl)-(2-hydroxyethyl)amino]ethanol;
5,6-dimethylpyrazole-[1,5-a]-pyrimidine-3,7-diamine;
2,6-dimethylpyrazole-[1,5-a]-pyrimidine-3,7-diamine;
2,5,N7,N7-tetramethylpyrazole-[1,5-a]-pyrimidine-3,7-diamine; and their physiologically compatible salts and their tautomeric forms if a tautomeric equilibrium is present.

The pyrazole-[1,5-a]-pyrimidines of the above formula (E4) can be prepared as described in the literature by cyclization starting from an aminopyrazole or from hydrazine.

The coupler components usually used are m-phenylenediamine derivatives, naphthols, resorcinol and resorcinol derivatives, pyrazolones and m-aminophenol derivatives. Suitable coupler substances are, in particular, 1-naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methyl-5-pyrazolone, 2,4-dichloro-3-aminophenol, 1,3-bis (2,4-diaminophenoxy)propane, 2-chlororesorcinol, 4-chlororesorcinol, 2-chloro-6-methyl-3-aminophenol, 2-amino-3-hydroxypyridine, 2-methylresorcinol, 5-methylresorcinol and 2-methyl-4-chloro-5-aminophenol.

Preferred coupler components according to the invention are:

m-aminophenol and its derivatives, such as, for example, 5-amino-2-methylphenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-(diethylamino)phenol, N-cyclopentyl-3-aminophenol, 1,3-dihydroxy-5-(methylamino)benzene, 3-(ethylamino)-4-methylphenol and 2,4-dichloro-3-aminophenol, o-aminophenol and derivatives thereof, m-diaminobenzene and derivatives thereof, such as, for example, 2,4-diaminophenoxyethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2-hydroxyethylamino)-1-methylbenzene and 1-amino-3-bis(2'-hydroxyethyl)aminobenzene, o-diaminobenzene and derivatives thereof, such as, for example, 3,4-diaminobenzoic acid and 2,3-diamino-1-methylbenzene, di- or trihydroxybenzene derivatives, such as, for example, resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene, pyridine derivatives, such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine and 3,5-diamino-2,6-dimethoxypyridine, naphthalene derivatives, such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene, morpholine derivatives, such as, for example, 6-hydroxybenzomorpholine and 6-aminobenzomorpholine, quinoxaline derivatives, such as, for example, 6-methyl-1,2,3,4-tetrahydroquinoxaline, pyrazole derivatives, such as, for example, 1-phenyl-3-methylpyrazol-5-one, indole derivatives, such as, for example, 4-hydroxyindole, 6-hydroxyindole and 7-hydroxyindole, pyrimidine derivatives, such as, for example, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine, or methylenedioxybenzene derivatives, such as, for example, 1-hydroxy-3,4-methylenedioxybenzene, 1-amino-3,4-methylenedioxybenzene and 1-(2'-hydroxyethyl)amino-3,4-methylenedioxybenzene.

Particularly preferred coupler components are 1-naphthol, 1,5-, 2,7- and 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol and 2,6-dihydroxy-3,4-dimethylpyridine.

It is not necessary for the oxidation dye precursors or the substantive dyes each to represent uniform compounds. Rather, as a consequence of the preparation processes for the individual dyes, the hair colorants according to the invention may also comprise further components in lesser amounts, provided these do not adversely affect the coloring result or do not have to be excluded for other reasons, e.g. toxicological reasons.

With regard to the dyes which can be used in the hair colorants and tints according to the invention, express reference is made to the monograph Ch. Zviak, The Science of Hair Care, Chapter 7 (pages 248–250; substantive dyes), and Chapter 8, pages 264–267; oxidation dye precursors), published as Volume 7 of the series "Dermatology" (Ed.: Ch., Culnan and H. Maibach), Verlag Marcel Dekker Inc., New York, Basle, 1986, and the "European Inventory of Cosmetic Raw Materials", published by the European Community, obtainable in floppy disk form from the Bundesverband Deutscher Industrie- und Handelsunternehmen für Arzneimittel, Reformwaren und Körperpflegemittel e.V., [Federal Association of German Industrial and Commercial Enterprises for Medicaments, Healthcare and Bodycare Products], Mannheim.

The oxidation dye precursors are present in the compositions according to the invention preferably in amounts of from 0.01 to 20% by weight, preferably 0.5 to 5% by weight, in each case based on the total composition.

The precursors of nature-analogous dyes used are preferably those indoles and indolines which have at least one hydroxyl or amino group, preferably as substituent on the 6-membered ring. These groups can carry further substituents, e.g. in the form of an etherification or esterification of the hydroxyl group or an alkylation of the amino group.

Particularly suitable precursors of nature-analogous hair dyes are derivatives of 5,6-dihydroxyindoline of the formula (Ia),

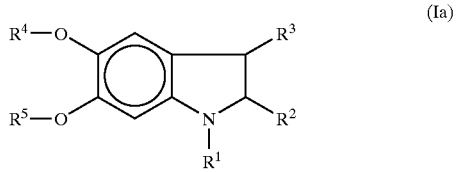

in which, independently of one another,
$R^1$ is hydrogen, a $C_1$–$C_4$-alkyl group or a $C_1$–$C_4$-hydroxyalkyl group,
$R^2$ is hydrogen or a —COOH group, where the —COOH group can also be in the form of a salt with a physiologically compatible cation,
$R^3$ is hydrogen or a $C_1$–$C_4$-alkyl group,
$R^4$ is hydrogen, a $C_1$–$C_4$-alkyl group or a group —CO—$R^6$ in which
$R^6$ is a $C_1$–$C_4$-alkyl group, and
$R^5$ is one of the groups given under $R^4$, and physiologically compatible salts of these compounds with an organic or inorganic acid.

Particularly preferred indoline derivatives are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, and 6-hydroxyindoline, 6-aminoindoline and 4-aminoindoline.

Within this group, particular preference is given to N-methyl-5,6-dihydroxyindoline, N-ethyl-5,6-dihydroxyindoline, N-propyl-5,6-dihydroxyindoline, N-butyl-5,6-dihydroxyindoline and, in particular, 5,6-dihydroxyindoline.

Also highly suitable precursors of nature-analogous hair dyes are derivatives of 5,6-dihydroxyindole of the formula (Ib),

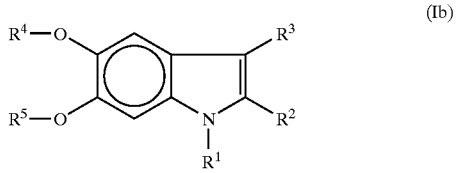

in which, independently of one another,
$R^1$ is hydrogen, a $C_1$–$C_4$-alkyl group or a $C_1$–$C_4$-hydroxyalkyl group,
$R^2$ is hydrogen or a —COOH group, where the —COOH group may also be in the form of a salt with a physiologically compatible cation,
$R^3$ is hydrogen or a $C_1$–$C_4$-alkyl group,
$R^4$ is hydrogen, a $C_1$–$C_4$-alkyl group or a group —CO—$R^6$, in which
$R^6$ is a $C_1$–$C_4$-alkyl group, and
$R^5$ is one of the groups given under $R^4$, and physiologically compatible salts of these compounds with an organic or inorganic acid.

Particularly preferred indole derivatives are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

Within this group, preference is given to N-methyl-5,6-dihydroxyindole, N-ethyl-5,6-dihydroxyindole, N-propyl-5,6-dihydroxyindole, N-butyl-5,6-dihydroxyindole and, in particular, 5,6-dihydroxyindole.

The indoline and indole derivatives can be used in the colorants used within the scope of the process according to the invention either as free bases or in the form of their physiologically compatible salts with inorganic or organic acids, e.g. the hydrochlorides, sulfates and hydrobromides. The indole or indoline derivatives are usually present therein in amounts of from 0.05–10% by weight, preferably 0.2–5% by weight.

When dye precursors of the indoline or indole type in particular are used, it has proven advantageous to use an amino acid and/or an oligopeptide as the alkalinizing agent.

For further shading, in addition to the dye precursors, the shaped bodies according to the invention may comprise substantive dyes. These are usually chosen from nitrophenylenediamines, nitroaminophenols, azo dyes, anthraquinones or indophenols. Preferred substantive dyes are the compounds known under the international names or trade names HC Yellow 2, HC Yellow 4, HC Yellow 5, HC Yellow 6, Basic Yellow 57, HC Orange 1, Disperse Orange 3, HC Red 1, HC Red 3, HC Red 13, HC Red BN, Basic Red 76, HC Blue 2, HC Blue 12, Disperse Blue 3, Basic Blue 7, Basic Blue 26, Basic Blue 99, HC Violet 1, Disperse Violet 1, Disperse Violet 4, Basic Violet 2, Basic Violet 14, Acid Violet 43, Disperse Black 9, Acid Black 52, Basic Brown 16 and Basic Brown 17, and 1,4-bis(β-hydroxyethyl)amino-2-nitrobenzene, 3-nitro-4-(β-hydroxyethyl)aminophenol, 4-amino-2-nitrodiphenylamine-2'-carboxylic acid, 6-nitro-1,2,3,4-tetrahydroquinoxaline, 2-hydroxy-1,4-naphthoquinone, hydroxyethyl-2-nitrotoluidine, picramic acid, 2-amino-6-chloro-4-nitrophenol, 4-ethylamino-3-nitrobenzoic acid and 2-chloro-6-ethylamino-1-hydroxy-4-nitrobenzene. The compositions according to the invention, according to this embodiment, comprise the substantive dyes preferably in an amount of from 0.01 to 20% by weight, based on the total colorant.

In addition, the preparations according to the invention can also comprise naturally occurring dyes, such as, for example, henna red, henna neutral, henna black, camomile blossom, sandalwood, black tea, buckthorn bark, sage, logwood, madder root, catechu, cedar and alkanna root.

Dissolution Accelerators

The shaped body according to the invention comprises, in a preferred embodiment of the present invention, a dissolution accelerator. The term dissolution accelerator covers here gas-evolving components, preformed and enclosed gases, disintegrants, and mixtures thereof.

In an embodiment of the present invention, gas-evolving components are used as dissolution accelerators. These components react together upon contact with water, with the in situ formation of gases which generate a pressure in the tablet, which causes the tablet to disintegrate into relatively small particles. One example of such a system are special combinations of suitable acids with bases. Preference is given to mono-, di- or trihydric acids with a $pK_a$ value of from 1.0 to 6.9. Preferred acids are citric acid, malic acid, maleic acid, malonic acid, itaconic acid, tartaric acid, oxalic acid, glutaric acid, glutamic acid, lactic acid, fumaric acid, glycolic acid, and mixtures thereof. Particular preference is given to citric acid. It may be very particularly preferred to use the citric acid in particulate form, the particles having a diameter of less than 1000 µm, in particular less than 700 µm, very particularly preferably less than 400 µm. Further alternative suitable acids are the homopolymers or copolymers of acrylic acid, maleic acid, methacrylic acid or itaconic acid with a molecular weight of from 2000 to 200 000. Particular preference is given to homopolymers of acrylic acid and copolymers of acrylic acid and maleic acid. According to the invention, preferred bases are alkali metal silicates, carbonates, hydrogencarbonates, and mixtures thereof. Metasilicates, hydrogencarbonates and carbonates are particularly preferred, and hydrogencarbonates are very particularly preferred. Particular preference is given to particulate hydrogencarbonates with a particle diameter of less than 1000 µm, in particular less than 700 µm, very particularly preferably less than 400 µm. Sodium or potassium salts of the abovementioned bases are particularly preferred. These gas-evolving components are present in the coloring shaped bodies according to the invention preferably in an amount of at least 10% by weight, in particular of at least 20% by weight.

In a further embodiment of the present invention, the gas is preformed or enclosed, meaning that as the shaped body starts to dissolve, gas starts to evolve and accelerate further dissolution. Examples of suitable gases are air, carbon dioxide, $N_2O$, oxygen and/or other nontoxic, noncombustible gases.

In a third, particularly preferred embodiment of the present invention, disintegration auxiliaries, termed shaped body disintegrants, are incorporated into the shaped bodies as dissolution accelerators in order to shorten the disintegration times. According to Römpp ($9^{th}$ Edition, Vol. 6, p. 4440) and Voigt "Lehrbuch der pharmazeutischen Technologie" [Handbook of pharmaceutical technology] ($6^{th}$ edition, 1987, pp. 182–184), shaped body disintegrants or disintegration accelerators are to be understood as meaning auxiliaries which provide for the rapid disintegration of shaped bodies in water or gastric juice and for the release of pharmaceuticals in resorbable form.

These substances, which are also referred to as disintegrants because of their action, increase their volume (swelling) as water enters. Swelling disintegration auxiliaries are, for example, synthetic polymers, such as polyvinylpyrrolidone (PVP) or natural polymers or modified natural substances, such as cellulose and starch and their derivatives, alginates or casein derivatives.

For the purposes of the present invention, preferred disintegration agents used are disintegration agents based on cellulose, meaning that preferred shaped bodies comprise such a disintegration agent based on cellulose in amounts of from 0.5 to 50% by weight, preferably 3 to 30% by weight, based on the overall shaped body. Pure cellulose has the formal empirical composition $(C_6H_{10}O_5)_n$ and, when considered formally, represents a β-1,4-polyacetal of cellobiose which in turn is constructed from two molecules of glucose. Suitable celluloses consist here of about 500 to 5000 glucose units and accordingly have average molar masses of from 50 000 to 500 000. For the purposes of the present invention, cellulose-based disintegration agents which can be used are also cellulose derivatives obtainable by polymer-analogous reactions from cellulose. Such chemically modified celluloses include here, for example, products from esterifications or etherifications in which hydroxyl hydrogen atoms have been substituted. However, celluloses in which the hydroxyl groups have been replaced by functional groups which are not bonded via an oxygen atom can also be used as cellulose derivatives. The group of cellulose derivatives includes, for example, alkali metal celluloses, carboxymethylcellulose (CMC), cellulose esters and ethers, and aminocelluloses. Said cellulose derivatives are preferably not used as single cellulose-based disintegration agents, but in a mixture with cellulose. The content of cellulose derivatives in these mixtures is preferably below 50% by weight, particularly preferably below 20% by weight, based on the cellulose-based disintegration agent. A particularly preferred cellulose-based disintegration agent used is pure cellulose which is free from cellulose derivatives.

The cellulose used as disintegration auxiliary is preferably not used in finely divided form, but converted to a more coarse form, for example granulated or compacted, before being added to the premixes to be compressed. The particle sizes of such disintegration agents are mostly above 200 µm, preferably to a degree of at least 90% by weight between 300 and 1600 µm and in particular to a degree of at least 90% by weight between 400 and 1200 µm. The disintegration auxiliaries according to the invention are, for example, available commercially under the name Arbocel® from Rettenmaier. A preferred disintegration auxiliary is, for example, Arbocel® TF-30-HG.

A further cellulose-based disintegration aid or constituent of this component used may be microcrystalline cellulose. This microcrystalline cellulose is obtained by partial hydrolysis of celluloses under conditions which only attack and completely dissolve the amorphous regions (about 30% of the overall cellulose mass) of the celluloses, but leave the crystalline regions (about 70%) undamaged. Subsequent disaggregation of the microfine celluloses which form as a result of the hydrolysis produces the microcrystalline celluloses which have primary particle sizes of about 5 µm and can be compacted, for example, to give granulates with an average particle size of 200 µm. Suitable microcrystalline cellulose is available commercially, for example, under the trade name Avicel®.

Accelerated dissolution of the shaped bodies can also be achieved according to the invention by pre-granulation of the other constituents of the shaped body.

Further Components

In addition to said ingredients, the shaped bodies according to the invention can also comprise all active ingredients, additives and auxiliaries known for such preparations. In many cases, the shaped bodies comprise at least one surfactant, both anionic and also zwitterionic, ampholytic, nonionic and cationic surfactants in principle being suitable. In many cases, it has, however, proven advantageous to choose the surfactants from anionic, zwitterionic or nonionic surfactants.

Anionic surfactants suitable in preparations according to the invention are all anionic surface-active substances suitable for use on the human body. These are characterized by a solubilizing, anionic group, such as, for example, a carboxylate, sulfate, sulfonate or phosphate group, and a lipophilic alkyl group having about 10 to 22 carbon atoms. Additionally, glycol or polyglycol ether groups, ester groups, ether groups and amide groups, and also hydroxyl groups, may be present in the molecule. Examples of suitable anionic surfactants are, in each case in the form of the sodium, potassium and ammonium and also the mono-, di- and trialkanolammonium salts with 2 or 3 carbon atoms in the alkanol group, linear fatty acids having 10 to 22 carbon atoms (soaps), ether carboxylic acids of the formula R—O—($CH_2$-$CH_2O$)$_x$—$CH_2$—COOH, in which R is a linear alkyl group having 10 to 22 carbon atoms and x=0 or 1 to 16, acyl sarcosides having 10 to 18 carbon atoms in the acyl group, acyl taurides having 10 to 18 carbon atoms in the acyl group, acyl isethionates having 10 to 18 carbon atoms in the acyl group, sulfosuccinic mono- and dialkyl esters having 8 to 18 carbon atoms in the alkyl group and sulfosuccinic monoalkyl polyoxyethyl esters having 8 to 18 carbon atoms in the alkyl group and 1 to 6 oxyethyl groups, linear alkanesulfonates having 12 to 18 carbon atoms, linear alpha-olefinsulfonates having 12 to 18 carbon atoms, alpha-sulfo fatty acid methyl esters of fatty acids having 12 to 18 carbon atoms, alkyl sulfates and alkyl polyglycol ether sulfates of the formula R—O($CH_2$—$CH_2O$)$_x$—$SO_3H$ in which R is a preferably linear alkyl group having 10 to 18 carbon atoms and x=0 or 1 to 12, mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids having 12 to 24 carbon atoms and 1 to 6 double bonds according to DE-A-39 26 344, esters of tartaric acid and citric acid with alcohols which represent addition products of about 2–15 molecules of ethylene oxide and/or propylene oxide onto fatty alcohols having 8 to 22 carbon atoms.

Preferred anionic surfactants are alkyl sulfates, alkyl polyglycol ether sulfates and ether carboxylic acids having 10 to 18 carbon atoms in the alkyl group and up to 12 glycol ether groups in the molecule, and in particular salts of saturated and in particular unsaturated $C_8$–$C_{22}$-carboxylic acids, such as oleic acid, stearic acid, isostearic acid and palmitic acid.

Noniogenic surfactants comprise, as hydrophilic group, e.g. a polyol group, a polyalkylene glycol ether group or a combination of polyol and polyglycol ether group. Such compounds are, for example, addition products of from 2 to 30 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group, $C_{12}$–$C_{22}$-fatty acid mono- and diesters of addition products of from 1 to 30 mol of ethylene oxide onto glycerol, $C_8$–$C_{22}$-alkyl mono- and oligoglycosides and ethoxylated analogs thereof, and addition products of from 5 to 60 mol of ethylene oxide onto castor oil and hydrogenated castor oil.

Preferred nonionic surfactants are alkyl polyglycosides of the general formula $R^1O$—$(Z)_x$. These compounds are, for example, available under the trade name Plantacare® from Henkel and are characterized by the following parameters.

The alkyl radical $R^1$ contains 6 to 22 carbon atoms and may either be linear or branched. Preference is given to primary linear radicals and aliphatic radicals methyl-branched in the 2-position. Such alkyl radicals are, for example, 1-octyl, 1-decyl, 1-lauryl, 1-myristyl, 1-cetyl and 1-stearyl. Particular preference is given to 1-octyl, 1-decyl, 1-lauryl, 1-myristyl. If "oxo alcohols" are used as starting materials, compounds with an uneven number of carbon atoms in the alkyl chain predominate.

The alkyl polyglycosides which can be used according to the invention can, for example, contain only one certain alkyl radical $R^1$. These compounds are usually, however, prepared starting from natural fats and oils or mineral oils. In this case, mixtures corresponding to the starting compounds or corresponding to the respective work-up of these compounds are present as alkyl radicals R.

Particular preference is given to those alkyl polyglycosides in which $R^1$ consists essentially of $C_8$- and $C_{10}$-alkyl groups, essentially of $C_{12}$- and $C_{14}$-alkyl groups, essentially of $C_8$- to $C_{16}$-alkyl groups or essentially of $C_{12}$- to $C_{16}$-alkyl groups.

Any desired mono- or oligosaccharides can be used as sugar building block Z. Sugars with 5 or 6 carbon atoms, and the corresponding oligosaccharides are usually used. Such sugars are, for example, glucose, fructose, galactose, arabinose, ribose, xylose, lyxose, allose, altrose, mannose, gulose, idose, talose and sucrose. Preferred sugar building blocks are glucose, fructose, galactose, arabinose and sucrose; glucose is particularly preferred.

The alkyl polyglycosides which can be used according to the invention contain, on average, 1.1 to 5 sugar units. Alkyl polyglycosides with x values of from 1.1 to 1.6 are preferred. Very particular preference is given to alkyl glycosides in which x is 1.1 to 1.4.

In addition to their surfactant action, the alkyl glycosides can also serve to improve the fixing of fragrance components to the hair. Thus, in cases where an action of the perfume oil on the hair beyond the duration of the hair treatment is desired, the person skilled in the art will thus preferably have recourse to this class of substance as a further ingredient of the preparations according to the invention. An alkyl glucoside which is particularly preferred according to the invention is the commercial product Plantacare® 1200G.

The alkoxylated homologues of said alkyl polyglycosides can also be used according to the invention. These homologues can contain, on average, up to 10 ethylene oxide and/or propylene oxide units per alkyl glycoside unit.

In addition, zwitterionic surfactants can be used, in particular as cosurfactants. Zwitterionic surfactants is the term used to describe those surface-active compounds which, in the molecule, carry at least one quaternary ammonium group and at least one —$COO^{(-)}$ or —$SO_3^{(-)}$ group. Particularly suitable zwitterionic surfactants are the betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines with in each case 8 to 18 carbon atoms in the alkyl or acyl group, and cocoacylaminoethyl hydroxyethylcarboxymethylglycinate. A preferred zwitterionic surfactant is the fatty acid amide derivative known under the INCI name Cocamidopropyl Betaine.

Likewise suitable as cosurfactants are ampholytic surfactants. Ampholytic surfactants is to be understood as meaning those surface-active compounds which, apart from a $C_8$–$C_{18}$-alkyl or acyl group in the molecule, contain at least one free amino group and at least one —COOH or —$SO_3$H group and are capable of forming internal salts. Examples of suitable ampholytic surfactants are N-alkylglycines, N-alkylpropionic acids, N-alkylaminobutyric acids, N-alkylaminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12-18}$-acylsarcosine.

According to the invention, the cationic surfactants used are in particular those of the quaternary ammonium compound type, of the esterquat type and of the amidoamine type.

Preferred quaternary ammonium compounds are ammonium halides, in particular chlorides and bromides, such as alkyltrimethylammonium chlorides, dialkyldimethylammonium chlorides and trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, and the imidazolium compounds known under the INCI names Quaternium-27 and Quaternium-83. The long alkyl chains of the abovementioned surfactants preferably have 10 to 18 carbon atoms.

The esterquats are known substances which contain both at least one ester function and also at least one quaternary ammonium group as structural element. Preferred esterquats are quaternized ester salts of fatty acids with triethanolamine, quaternized ester salts of fatty acids with diethanolalkylamines and quaternized ester salts of fatty acids with 1,2-dihydroxypropyldialkylamines. Such products are sold, for example, under the tradenames Stepantex®, Dehyquart® and Armocare®. The products Armocare® VGH-70, an N,N-bis(2-palmitoyloxyethyl)dimethylammonium chloride, and Dehyquart® F-75 and Dehyquart® AU-35 are examples of such esterquats.

The alkylamidoamines are usually prepared by amidation of natural or synthetic fatty acids and fatty acid fractions with dialkylaminoamines. A particularly suitable compound from this group of substances according to the invention is the stearamidopropyldimethylamine available commercially under the name Tegoamid® S 18.

Further cationic surfactants which can be used according to the invention are the quaternized protein hydrolyzates.

Likewise suitable according to the invention are cationic silicone oils, such as, for example, the commercially available products Q2-7224 (manufacturer: Dow Corning; a stabilized trimethylsilylamodimethicone), Dow Corning 929 emulsion (comprising a hydroxylamino-modified silicone, which is also referred to as amodimethicones), SM-2059 (manufacturer: General Electric), SLM-55067 (manufacturer: Wacker) and Abil®-Quat 3270 and 3272 (manufacturer: Th. Goldschmidt; diquaternary polydimethylsiloxanes, Quaternium-80).

An example of a quaternary sugar derivative which can be used as cationic surfactant is the commercial product Glucquat®100, according to INCI nomenclature a "Lauryl Methyl Gluceth-10 Hydroxypropyl Dimonium Chloride".

The compounds containing alkyl groups used as surfactant may in each case be uniform substances. However, it is generally preferred to start from native vegetable or animal raw materials in the preparation of these substances, meaning that substance mixtures with varying alkyl chain lengths, depending on the raw material in question, are obtained.

In the case of the surfactants which are addition products of ethylene oxide and/or propylene oxide with fatty alcohols or derivatives of these addition products, it is possible to use either products with a "normal" homologue distribution or those with a narrowed homologue distribution. "Normal" homologue distribution is understood as meaning here mixtures of homologues obtained during the reaction of fatty alcohol and alkylene oxide using alkali metals, alkali metal hydroxides or alkali metal alkoxides as catalysts. By contrast, narrowed homologue distributions are obtained when, for example, hydrotalcites, alkaline earth metal salts of ether carboxylic acids, alkaline earth metal oxides, hydroxides or alkoxides are used as catalysts. The use of products with narrowed homologue distribution may be preferred.

Furthermore, the shaped bodies according to the invention may preferably also comprise a conditioning active ingredient chosen from the group formed by cationic surfactants, cationic polymers, alkylamidoamines, paraffin oils, vegetable oils and synthetic oils. With regard to the cationic surfactants, reference may be made to the above statements.

Cationic polymers may be preferred as conditioning active ingredients. These are usually polymers which contain a quaternary nitrogen atom, for example in the form of an ammonium group. Preferred cationic polymers are, for example,

- quaternized cellulose derivatives, as are commercially available under the names Celquat® and Polymer JR®. The compounds Celquat® H 100, Celquat® L 200 and Polymer JR®400 are preferred quaternized cellulose derivatives.
- polymeric dimethyldiallylammonium salts and copolymers thereof with acrylic acid and esters and amides of acrylic acid and methacrylic acid. The products commercially available under the names Merquat®100 (poly(dimethyldiallylammonium chloride)), Merquat®550 (dimethyldiallylammonium chloride-acrylamide copolymer) and Merquat®280 (dimethyldiallylammonium chloride/acrylic acid copolymer are examples of such cationic polymers.
- copolymers of vinylpyrrolidone with quaternized derivatives of dialkylaminoacrylate and -methacrylate, such as, for example, vinylpyrrolidone-dimethylaminomethacrylate copolymers quaternized with diethyl sulfate. Such compounds are commercially available under the names Gafquat®734 and Gafquat®755.
- vinylpyrrolidone-methoimidazolinium chloride copolymers, as supplied under the name Luviquat®.
- quaternized polyvinyl alcohol and the polymers known under the names
- polyquaternium 2,
- polyquaternium 17,
- polyquaternium 18 and
- polyquaternium 27 with quaternary nitrogen atoms in the polymer main chain.

Particular preference is given to cationic polymers of the four first-named groups, and very particular preference is given to polyquaternium-2, polyquaternium-10 and polyquaternium-22.

Also suitable as conditioning active ingredients are silicone oils, in particular dialkyl- and alkylarylsiloxanes, such as, for example, dimethylpolysiloxane and methylphenylpolysiloxane, and alkoxylated and quaternized analogs thereof. Examples of such silicones are the products sold by Dow Corning under the names DC 190, DC 200, DC 344, DC 345 and DC 1401, and the commercial products Q2-7224 (manufacturer: Dow Corning; a stabilized trimethylsilylamodimethicone), Dow Corning® 929 emulsion (comprising a hydroxylamino-modified silicone which is also referred to as Amodimethicone), SM-2059 (manufacturer: General Electric), SLM-55067 (manufacturer: Wacker) and Abil®-Quat 3270 and 3272 (manufacturer: Th. Goldschmidt; diquaternary polydimethylsiloxane, quaternium-80).

As conditioning active ingredients it is also possible to use paraffin oils, synthetically prepared oligomeric alkenes and vegetable oils such as jojoba oil, sunflower oil, orange oil, almond oil, wheatgerm oil and peach kernel oil.

Likewise suitable hair-conditioning compounds are phospholipids, for example soybean lecithin, egg lecithin and cephalins.

Furthermore, the preparations used according to the invention preferably comprise at least one oil component.

Oil components suitable according to the invention are, in principle, all water-insoluble oils and fatty substances and mixtures thereof with solid paraffins and waxes. Water-insoluble is used according to the invention to define substances whose solubility in water is less than 0.1% by weight at 20° C.

A preferred group of oil components are vegetable oils. Examples of such oils are sunflower oil, olive oil, soybean oil, rapeseed oil, almond oil, jojoba oil, orange oil, wheatgerm oil, peach kernel oil and the liquid fractions of coconut oil.

Also suitable, however, are other triglyceride oils, such as the liquid fractions of beef tallow and synthetic triglyceride oils.

A further, particularly preferred group of compounds which can be used according to the invention as oil component are liquid paraffin oils and synthetic hydrocarbon and di-n-alkyl ethers with a total of between 12 and 36 carbon atoms, in particular 12 and 24 carbon atoms, such as, for example, di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether and di-tert-butyl ether, diisopentyl ether, di-3-ethyldecyl ether, tert-butyl n-octyl ether, isopentyl n-octyl ether and 2-methylpentyl n-octyl ether. The compounds 1,3-di(2-ethylhexyl)cyclohexane (Cetiol® S) and di-n-octyl ether (Cetiol® OE), which are available as commercial products, may be preferred.

Oil components which can likewise be used according to the invention are fatty acid and fatty alcohol esters. Preference is given to the monoesters of fatty acids with alcohols having 3 to 24 carbon atoms. This group of substances includes the products of the esterification of fatty acids having 6 to 24 carbon atoms, such as, for example, caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachidic acid, gadoleic acid, behenic acid and erucic acid, and technical-grade mixtures thereof which are produced, for example, during the pressurized cleavage of natural fats and oils, the oxidation of aldehydes from the Roelen oxo synthesis or the dimerization of unsaturated fatty acids, with alcohols such as, for example, isopropyl alcohol, caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol, and technical-grade mixtures thereof which are produced, for example, during the high-pressure hydrogenation of technical-grade methyl esters based on fats and oils or aldehydes from the Roelen oxo synthesis, and as monomer fraction during the dimerization of unsaturated fatty alcohols. According to the invention, isopropyl myristate, C16–18-alkyl isononoate (Cetiol® SN), 2-ethylhexyl stearate (Cetiol® 868), cetyl oleate, glycerol tricaprylate, coconut fatty alcohol caprate/caprylate and n-butyl stearate are particularly preferred.

Furthermore, dicarboxylic esters, such as di-n-butyl adipate, di(2-ethylhexyl) adipate, di(2-ethylhexyl) succinate and diisotridecyl acelate, and diol esters, such as ethylene glycol dioleate, ethylene glycol diisotridecanoate, propylene glycol di(2-ethyl hexanoate), propylene glycol diisostearate, propylene glycol dipelargonate, butanediol diisostearate and neopentylglycol dicaprylate also represent oil components which can be used according to the invention, as do complex esters, such as, for example, diacetyl glycerol monostearate.

Finally, it is also possible to use fatty alcohols having 8 to 22 carbon atoms as oil components effective according to the invention. The fatty alcohols may be saturated or unsaturated and linear or branched. For the purposes of the invention it is possible to use, for example, decanol, octanol, octenol, dodecenol, decenol, octadienol, dodecadienol, decadienol, oleyl alcohol, erucic alcohol, ricinoleic alcohol, stearyl alcohol, isostearyl alcohol, cetyl alcohol, lauryl alcohol, myristyl alcohol, arachidyl alcohol, caprylic alcohol, capric alcohol, linoleyl alcohol, linolenyl alcohol and behenyl alcohol, and Guerbet alcohols thereof, the intention being for this list to be exemplary and nonlimiting. However, the fatty alcohols originate from preferably natural fatty acids, it usually being possible to start from an isolation from the esters of the fatty acids by reduction. Those fatty alcohol fractions which are produced by reduction of naturally occurring triglycerides, such as beef tallow, palm oil, peanut oil, rapeseed oil, cottonseed oil, soybean oil, sunflower oil and linseed oil or fatty acid esters formed from their transesterification products with corresponding alcohols, and also a mixture of different fatty alcohols can likewise be used according to the invention.

The oil components are preferably used in amounts of from 0.05 to 10% by weight, in particular from 0.1 to 2% by weight, in the shaped bodies according to the invention.

In a preferred embodiment of the present invention, upon dissolution of the shaped bodies in water, a gel forms. For this purpose, thickeners such as agar agar, guar gum, alginates, xanthan gum, gum arabic, karaya gum, carob seed grain, linseed gums, dextrans, cellulose derivatives, e.g. methylcellulose, hydroxyalkylcellulose and carboxymethylcellulose, starch fractions and derivatives such as amylose, amylopectin and dextrins, clays, such as, for example, bentonite, silicates as sold, for example, under the trade names Optigel® (Süd-Chemie) or Laponite® (Solvay), or fully synthetic hydrocolloids, such as e.g. polyvinyl alcohol, are added to the shaped body. Particularly preferred thickeners are xanthans, alginates and highly substituted carboxymethylcelluloses.

Further active ingredients, auxiliaries and additives are, for example, zwitterionic and amphoteric polymers, such as, for example, acrylamidopropyltrimethylammonium chloride/acrylate copolymers and octylacrylamide/ methyl methacrylate/tert-butylaminoethyl methacrylate/2-hydroxypropyl methacrylate copolymers, anionic polymers, such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butylacrylamide terpolymers, structurants, such as maleic acid and lactic acid, protein hydrolyzates, in particular the hydrolyzates of elastin, collagen, keratin, milk protein, soybean protein and wheat protein, the condensation products thereof with fatty acids, and quaternized protein hydrolyzates, perfume oils, dimethyl isosorbide and cyclodextrins, solvents and solubility promoters, such as ethylene glycol, propylene glycol, glycerol and diethylene glycol, fiber structure-improving active ingredients, in particular mono-, di- and oligosaccharides, such as, for example, glucose, galactose, fructose, fruit sugars and lactose, quaternized amines, such as methyl-1-alkylamido-ethyl-2-alkylimidazolinium methosulfate antifoams, such as silicones, dyes for coloring the agent, antidandruff active ingredients, such as piroctone olamine, zinc omadine and climbazole, light protection agents, in particular derivatized benzophenones, cinnamic acid derivatives and triazines, substances for adjusting the pH, such as, for example, customary acids, in particular food acids and bases active ingredients, such as allantoin, pyrrolidonecarboxylic acids and salts thereof, and bisabolol, vitamins, provitamins and vitamin precursors, in particular those of groups A, $B_3$, $B_5$, $B_6$, C, E, F and H, plant extracts, such as the extracts from green tea, oak bark, stinging nettle, hamamelis, hops, chamomile, burdock, horsetail, hawthorn, lime blossom, almond, aloe vera, spruce needle, horse chestnut, sandalwood, juniper, coconut, mango, apricot, lime, wheat, kiwi, melon, orange, grapefruit, sage, rosemary, birch, mallow, lady's smock, wild thyme, yarrow, thyme, balm, restharrow, coltsfoot, marshmallow, meristem, ginseng and root ginger, cholesterol, bodying agents, such as sugar esters, polyolesters or polyol alkyl ethers, fats and waxes, such as spermaceti, beeswax, montan wax and paraffins, fatty acid alkanolamides, complexing agents, such as EDTA, NTA, β-alaninediacetic acid and phosphonic acids, swelling and penetration substances, such as glycerol, propylene glycol monoethyl ether, carbonates, hydrogencarbonates, guanidines, ureas and primary, secondary and tertiary phosphates, opacifiers, such as latex, styrene/PVP and styrene/acrylamide copolymers, pearlizing agents, such as ethylene glycol mono- and distearate, and PEG-3 distearate, pigments, stabilizing agents for the oxidizing agent, antioxidants.

With regard to further optional components and the amounts of these components used, reference is expressly made to the relevant handbooks known to the person skilled in the art, e.g. Kh. Schrader, Grundlagen und Rezepturen der Kosmetika [Cosmetic Formulations and Bases], 2nd edition, Hüthig Buch Verlag, Heidelberg, 1989.

It may also be preferred according to the invention to encapsulate separately individual active ingredients prior to their incorporation into the shaped bodies; thus, it is, for example, conceivable to use particularly reactive components or else the fragrances in encapsulated form.

Shaped Body Geometries

The shaped bodies according to the invention can assume any geometric shape, such as, for example, concave, convex, biconcave, biconvex, cubic, tetragonal, orthorhombic, cylindrical, spherical, cylinder-segment-like, discoid, tetrahedral, dodecahedral, octahedral, conical, pyramidal, ellipsoid, pentagon-, hectagon- and octagon-prismatic, and rhombohedral shapes. It is also possible to realize entirely irregular areas, such as arrow or animal shapes, trees, clouds, etc. Formation as bars, rods or ingots, cubes, blocks and corresponding three-dimensional elements having planar side faces, and in particular cylindrical designs with a circular or oval cross section are preferred according to the invention. This cylindrical design covers here forms ranging from tablets to compact cylinder sections with a height to diameter ratio of more than 1. If the basic shaped body has corners and edges, then these are preferably rounded off. As additional visual differentiation, an embodiment having rounded corners and beveled ("chamfered") edges is preferred.

In a first preferred embodiment, the portioned compacts can in each case be designed as an individual element separate from the others which corresponds to the predetermined dosage amount of the colorant and/or the oxidizing agent. Likewise, however, it is possible to design compacts which combine a plurality of such mass units in one compact, the provision for portioned smaller units to be readily separated off being in particular by means of pre-given breakage points. The design of the portioned compacts as tablets in cylinder or block form may be advantageous where a diameter/height ratio in the range from about 0.5:2 to 2:0.5 is preferred. Commercially available hydraulic presses, eccentric presses or rotary presses, in particular, are suitable devices for the preparation of such compacts.

The preferred three-dimensional shape of the shaped bodies according to the invention has a rectangular base, where the height of the shaped body is less than the smaller rectangular side of the base. Rounded corners are preferred in this supply form.

A further preferred shaped body which can be prepared has a plate-like or bar-like structure with alternating long thick and short thin segments, so that individual segments can be broken off from this "slab" at the intended breakage points, which represent the short thin segments, and can be used in this way in portions. This principle of the "slab-like" shaped body can also be realized in other geometric shapes, for example vertical triangles connected to one another along only one of their sides.

In a second preferred embodiment, the various components are not compressed to give a uniform tablet, but during tableting shaped bodies are obtained which have two or more layers, i.e. at least two layers. In this connection, it is also possible for these various layers to have different dissolution rates. Advantageous performance properties of the shaped bodies may result from this. If, for example, components are present in the shaped bodies which have a mutually negative effect, then it is possible to integrate one component into the more rapidly dissolving layer and to incorporate the other component into a more slowly dissolving layer so that the components do not react with one another during the dissolution operation.

According to the invention, it is particularly preferred if the shaped bodies consist of at least three layers, a first layer (A) comprising the dye preparation and the alkalinizing agent, a second layer (B) representing an inert interlayer and a third layer (C) comprising the oxidizing agent preparation.

The layer structure of the shaped bodies can either be stack-like, where a dissolution process of the internal layer (s) takes place at the edges of the shaped body if the outer layers have still not completely dissolved. A preferred stacking sequence is (A), (B), (C). In the case of the stack-like arrangement, the stack axis can be arranged as desired relative to the tablet axis. The stacking axis can thus, for example in the case of a cylindrical tablet, be parallel or perpendicular to the height of the cylinder.

However, according to a further embodiment, it may also be preferred if complete coverage of the internal layer(s) by the outer layer(s) is achieved, which leads to prevention of premature dissolution of constituents of the internal layer(s). Preference is given to shaped bodies in which the layer (A) is completely covered by the layer (B) and this in turn is completely covered by the layer (C). Likewise, shaped bodies may be preferred in which the layer (C) is completely covered by the layer (B) and this in turn is completely covered by the layer (A).

Similar effects can also be achieved by coating individual constituents of the composition to be compressed or of the overall shaped body. In this connection, the bodies to be coated can, for example, be sprayed with aqueous solutions or emulsions, or else a coating can be obtained by means of the process of hot-melt coating.

Following compression, the shaped bodies have high stability. The fracture strength of cylindrical shaped bodies can be ascertained by means of the parameter of diametral fracture stress. This diametral fracture stress can be determined by $$\sigma = \frac{2P}{\pi Dt}$$

where σ represents the diametral fracture stress (DFS) in Pa, P is the force in N which leads to the pressure exerted on the shaped body, which pressure causes the fracture of the tablet, D is the diameter of the shaped body in meters, and t is the height of the shaped body.

The shaped bodies of the present invention advantageously have a density of from 0.3 g/cm$^3$ to 2.0 g/cm$^3$, in particular from 0.5 g/cm$^3$ to 1.1 g/cm$^3$.

In a third preferred embodiment, the shaped bodies according to the invention consist of a shaped body prepared per se by known tableting operations and described by the term "basic shaped body" which has a depression. Preferably, the basic shaped body is firstly prepared and the further compressed part is introduced onto or into this basic shaped body in a further processing step. The resulting product is referred to below by the general term "depression shaped body" or "depression tablet".

According to the invention, the basic shaped body can in principle assume all realizable three-dimensional shapes. Particular preference is given to the three-dimensional shapes already given above. The shape of the depression can be freely chosen, preference being given, according to the invention, to shaped bodies in which at least one depression can assume a concave, convex, cubic, tetragonal, orthorhombic, cylindrical, spherical, cylinder-segmentlike, discoid, tetrahedral, dodecahedral, octahedral, conical, pyramidal, ellipsoid, pentagon-, heptagon- and octagon-prismatic and rhombohedral forms. It is also possible to realize completely irregular depression shapes, such as arrow or animal shapes, trees, clouds, etc. As with the base shaped bodies, depressions with rounded corners and edges or with rounded corners and beveled edges are preferred.

The size of the depression relative to the overall shaped body is governed by the desired intended use of the shaped body. Depending on whether a smaller or larger amount of active substance is to be present in the second compressed part, the size of the depression may vary. Irrespective of the intended use, preference is given to shaped bodies in which the weight ratio of basic shaped body to depression filling is within the range from 1:1 to 100:1, preferably from 2:1 to 80:1, particularly preferably from 3:1 to 50:1 and in particular from 4:1 to 30:1.

Similar statements can be made as regards the surface area fractions accounted for by the basic shaped body and by the depression filling of the total surface area of the shaped body. In this case, preference is given to shaped bodies in which the surface area of the impressed depression filling constitutes 1 to 25%, preferably 2 to 20%, particularly preferably 3 to 15% and in particular 4 to 10% of the total surface area of the filled basic shaped body.

If, for example, the total shaped body has dimensions of 20×20×40 mm and thus a total surface area of 40 cm$^2$, then preference is given to depression fillings which have a surface area of from 0.4 to 10 cm$^2$, preferably 0.8 to 8 cm$^2$, particularly preferably from 1.2 to 6 cm$^2$ and in particular from 1.6 to 4 cm$^2$.

The depression filling and the basic shaped body are preferably colored so as to be visually distinguishable. In addition to the visual differentiation, depression tablets have performance advantages on the one hand as a result of different solubilities of the different regions, but on the other hand also as a result of the separate storage of the active ingredients in the different regions of the shaped body.

Shaped bodies in which the impressed depression filling dissolves more slowly than the basic shaped body are preferred according to the invention. By incorporating certain constituents, on the one hand, it is possible to vary the solubility of the depression filling in a targeted manner; secondly, the release of certain ingredients from the depression filling may lead to advantages in the coloring process. Ingredients which are preferably localized, at least proportionately, in the depression filling are, for example, the conditioning active ingredients, oily substances, vitamins and plant active ingredients described below.

Tableting

The shaped bodies according to the invention are prepared by firstly dry-mixing the constituents, some or all of which may have been pregranulated, and subsequently shaping the mixture, in particular by compression to give tablets, in which context it is possible to have recourse to known processes. To prepare the shaped bodies according to the invention, the premix is compacted in a "die" between two punches to form a solid compact. This operation, which is referred to below for short as tableting, is divided into four sections; metering, compaction (elastic deformation), plastic deformation and ejection.

Firstly, the premix is introduced into the die, the fill level and thus the weight and the shape of the resulting shaped body being determined by the position of the lower punch and by the shape of the compression tool. Even in the case of high shaped body throughput, constant metering is preferably achieved by volumetric metering of the premix. In the subsequent course of tableting, the upper punch contacts the premix and is lowered further in the direction of the lower punch. In the course of this compaction, the particles of the premix are pressed closer to one another, with a continual reduction in the void volume within the filling between the punches. When the upper punch reaches a certain position (and thus when a certain pressure is acting on the premix), plastic deformation begins in which the particles coalesce and the shaped body forms. Depending on the physical properties of the premix, a portion of the premix particles is also crushed and at even higher pressures there is sintering of the premix. With an increasing compression rate, i.e. high throughputs, the phase of elastic deformation becomes shorter and shorter, with the result that the shaped bodies which form may have larger or smaller voids. In the final step of tableting, the finished shaped body is ejected from the die by the lower punch and conveyed away by means of downstream transport means. At this point in time, it is only the weight of the shaped body which has been ultimately defined, since the compacts may still change their shape and size as a result of physical processes (elastic relaxation, crystallographic effects, cooling, etc.).

Tableting is carried out in standard commercial tableting presses, which may in principle be equipped with single or double punches. In the latter case, pressure is built up not only using the upper punch, but the lower punch as well moves toward the upper punch during the compression operation, while the upper punch presses downward. For small production volumes it is preferred to use eccentric tableting presses in which the punch or punches is/are attached to an eccentric disk, which in turn is mounted on an axle having a defined speed of rotation. The movement of these compression punches is comparable with the way in which a customary four-stroke engine works. Compression can take place with one upper and one lower punch, or else a plurality of punches may be attached to one eccentric disk, the number of die bores being increased correspondingly. The throughputs of eccentric presses vary, depending on the model, from several hundred up to a maximum of 3000 tablets per hour.

For greater throughputs, the presses chosen are rotary tableting presses in which a relatively large number of dies is arranged in a circle on a "die table". Depending on the model, the number of dies varies between 6 and 55, larger dies also being available commercially. Each die on the die table is allocated an upper punch and a lower punch, it being possible again for the compressive pressure to be built up actively by the upper punch or lower punch only, or else by both punches. The die table and the punches move around a common vertical axis, and during rotation the punches, by means of rail-like cam track, are brought into the position for filling, compaction, plastic deformation and ejection. At those sites where considerable raising or lowering of the punches is necessary (filling, compaction, ejection), these cam tracks are assisted by additional low-pressure actions, low tension rails and discharge tracks. The die is filled by way of a rigid supply means, the "filling shoe", which is connected to a storage vessel for the premix. The compressive force on the premix can be adjusted individually for upper punch and lower punch by way of compression paths, the pressure being built up by the rolling movement of the punch shaft heads past displaceable pressure rolls.

In order to increase the throughput, rotary presses may also be provided with two filling shoes, where only one half-circle need be traveled to produce one tablet. For the production of two-layer and multilayer shaped bodies, a plurality of filling shoes are arranged in series, and the gently pressed first layer is not ejected before further filling. By means of an appropriate process regime, it is possible in this way to produce coated tablets and inlay tablets as well, having a construction like that of an onion skin, in the case of the inlay tablet the top face of the core or of the core layers is not covered and therefore remains visible. Rotary tableting presses can also be equipped with single or multiple tools, so that, for example, an outer circle with 50 bores and an inner circle with 35 bores can be used simultaneously for compression. The throughputs of modern rotary tableting presses amount to more than one million shaped bodies per hour.

When tableting with rotary presses, it has proven advantageous to carry out tableting with minimal fluctuations in tablet weight. Fluctuations in tablet hardness can also be reduced in this way. Slight fluctuations in weight can be achieved as follows:

use of plastic inserts with small thickness tolerances low rotor speed large filling shoes matching of the rotary speed of the filling shoe wing to the speed of the rotor filling shoe with constant powder height decoupling of filling shoe and powder charge To reduce caking on the punches, all of the antiadhesion coatings known from the art are available. Plastic coatings, plastic inserts or plastic punches are particularly advantageous. Rotating punches have also proven advantageous in which case, where possible, upper punch and lower punch should be of rotatable configuration. In the case of rotating punches, it is generally possible to dispense with a plastic insert. In this case the punch surfaces should be electropolished.

It has also been found that long compression times are advantageous. These times can be established using pressure rails, a plurality of pressure rolls, or low rotor speeds. Since the fluctuations in tablet hardness are caused by fluctuations in the compressive forces, systems should be employed which limit the compressive force. In this case, it is possible to use elastic punches, pneumatic compensators, or sprung elements in the force path. In addition, the pressure roll may be of sprung design.

Tableting machines suitable for the purposes for the present invention are available, for example, from the following companies: Apparatebau Holzwarth GbR, Asperg, Wilhelm Fette GmbH, Schwarzenbek, Fann Instruments Company, Houston, Tex. (USA), Hofer GmbH, Weil, Horn & Noack Pharmatechnik GmbH, Worms, IMA Verpackungssysteme GmbH Viersen, KILIAN, Köln, KOMAGE, Kell am See, KORSCH Pressen AG, Berlin, and also Romaco GmbH, Worms. Examples of further suppliers are Dr. Herbert Pete, Vienna (AT), Mapag Maschinenbau AG, Bern (CH), BWI Manesty, Liverpool (GB), I. Holand Ltd., Nottingham (GB), Courtoy N. V., Halle (BE/LU) and also Mediopharm Kamnik (SI). A particularly suitable apparatus is, for example, the hydraulic double-pressure press HPF 630 from LAEIS, D. tableting tools are available, for example, from the following companies: Adams Tablettierwerkzeuge, Dresden, Wilhelm Fett GmbH, Schwarzenbek, Klaus Hammer, Solingen, Herber % Söhne GmbH, Hamburg, Hofer GmbH, Weil, Horn & Noack, Pharmatechnik GmbH, Worms, Ritter Pharamatechnik GmbH, Hamburg, Romaco, GmbH, Worms and Notter Werkzeugbau, Tamm. Further suppliers are, for example, Senss AG, Reinach (CH) and Medicopharm, Kamnik (SI).

However, the process for the preparation of the shaped bodies is not limited to compressing only one particulate premix to give a shaped body. Rather, the process may also be extended to the effect that, in a manner known per se, multilayer shaped bodies are produced by preparing two or more premixes which are compressed one on top of the other. Here, the first premix introduced is slightly precompressed in order to acquire a smooth top face which extends parallel to the shaped body base, and, after the second premix has been introduced, final compression takes place to give the finished shaped body. In the case of shaped bodies with three or more layers, there is a further precompression following the addition of each premix before the shaped body, after the addition of the last premix, undergoes final compression.

The compression of the particulate composition into the depression may take place in analogy to the production of the basic shaped body on tableting presses. Preference is given to a procedure in which first the base tablet including depression is produced, then filled and subsequently compressed again. This can be done by ejecting the base shaped bodies from a first tableting press, filling them, and transporting them to a second tableting press in which final compression takes place. Alternatively, final compression may also take place by means of pressure rolls which roll over the shaped bodies situated on a conveyor belt. It is, however, also possible to provide a rotary tableting press with different sets of punches, so that a first set of punches impresses indentations into the shaped bodies and the second set of punches, after filling, ensures a planar surface of the shaped body by means of postcompression.

Packaging

As described above, the shaped bodies prepared according to the invention can be provided in whole or in part with a coating. Processes in which an aftertreatment consists in applying a coating layer to the surface(s) of the shaped bodies in which the filled depression(s) is (are) located, or in applying a coating layer to the entire shaped body are preferred in accordance with the invention.

Following production, the shaped bodies according to the invention may be packaged, the use of certain packaging systems having proven particularly useful since these packaging systems on the one hand increase the storage stability of the ingredients but on the other hand also, if appropriate, improve markedly the long-term adhesion of the depression filling. The term "packaging system" always characterizes for the purposes of the present invention the primary packaging of the shaped body, i.e. the packaging whose inside is in direct contact with the surface of the shaped body. No requirements of any kind are placed on an optional secondary packaging, meaning that all customary materials and systems can be used here.

According to the invention, preference is given to packaging systems which have only a low moisture transmission rate. In this way, the coloring ability of the shaped bodies according to the invention can be retained over a prolonged period, even if, for example, hygroscopic components are used in the shaped bodies. Particular preference is given to packaging systems which have a moisture vapor transmission rate of from 0.1 g/m²/day to less than 20 g/m²/day if the packaging system is stored at 23° C. and a relative equilibrium humidity of 85%. Said temperature and humidity conditions are the test conditions specified in DIN Standard 53122, which allows minimal deviations (23±1° C., 85±2% relative humidity). The moisture vapor transmission rate of a given packaging system or material can be determined in accordance with further standard methods and is also described, for example, in ASTM Standard E-96-53T ("Test for measuring water vapor transmission of materials in sheet form") and in the TAPPI Standard T464 m-45 ("Water vapor permeability of sheet materials at high temperature and humidity"). The measurement principle of common techniques is based on the water absorption of anhydrous calcium chloride which is stored in a container in the appropriate atmosphere, the container being closed at the top face with the material to be tested. From the surface area of the container closed with the material to be tested (permeation area), the weight increase of the calcium chloride, and the exposure time, it is possible to calculate the moisture vapor transmission rate as follows:

$$FDDR = \frac{24 \cdot 10000}{A} \cdot \frac{x}{y} \ [g/m^2/24 \ h]$$

where A is the area of the material to be tested in cm², x is the increase in weight of the calcium chloride in g and y is the exposure time in h.

The relative equilibrium humidity, often referred to as "relative atmospheric humidity" is 85% at 23° C. when the moisture vapor transmission rate is measured in the context of the present invention. The ability of air to absorb water vapor increases with temperature up to a particular maximum content, termed the saturation content, and is specified in g/m³. For example, 1 m³ of air at 17° is saturated with 14.4 g of water vapor, at a temperature of 11°, saturation is reached with just 10 g of water vapor. The relative atmospheric humidity is the ratio of the water vapor content actually present to the saturation content at the prevailing temperature, expressed as a percentage. If, for example, air at 17° contains 12 g/m³ of water vapor, in the relative atmospheric humidity (RH)=(12/14.4)·100=83%. If this air is cooled, then saturation (100% RH) is reached at what is known as the dew point (in the example: 14°), i.e., on further cooling a precipitate is formed in the form of a mist (dew). The humidity is determined quantitatively using hygrometers and psychrometers.

The relative equilibrium humidity of 85% at 23° C. can be established precisely, for example, in laboratory chambers with humidity control, to +/−2% RH depending on the type of apparatus. In addition, constant and well-defined relative atmospheric humidities are formed in closed systems at a given temperature over saturated solutions of certain salts, these humidities deriving from the phase equilibrium between partial pressure of the water, saturated solution and sediment.

The combinations of shaped bodies and packaging system may of course for their part be packaged in secondary packaging, for example cartons or trays; no further requirements need be imposed on the secondary packaging. Accordingly, the secondary packaging is possible but not necessary.

Depending on the embodiment of the invention, the packaging system includes one or more shaped bodies. According to the invention, it is preferred either to design a shaped body in such a way that it comprises one application unit of the colorant, and to package this shaped body individually, or to pack into one packaging unit the number of shaped bodies which totals one application unit. This principle can of course be extended so that, in accordance with the invention, combinations may also comprise three, four, five or even more shaped bodies in one packaging unit. Two or more shaped bodies in one package can of course have different compositions. In this way it is possible to spatially separate certain components from one another in order, for example, to avoid stability problems.

The packaging system of the combination according to the invention may consist of a very wide variety of materials and may assume any desired external shapes. For cost reasons and for reasons of greater ease of processing, however, preference is given to packaging systems in which the packaging material has a low weight, is easy to process and is compatible in a cost-effective and ecological manner.

In a first combination as preferred according to the invention, the packaging system consists of a bag or pouch of single-layer or laminated paper and/or polymer film. In this connection, the shaped bodies may be filled unsorted, i.e. as a loose heap, into a pouch made of said materials. However, for aesthetic reasons and for sorting the combinations into secondary packagings, it is preferred to fill the shaped bodies individually, or sorted into groups of two or more, into bags or pouches. These packaging systems may then optionally—again, preferably sorted—be packaged into outer packagings which emphasizes the compact supply form of the shaped body.

The bags or pouches made of single-layer or laminated paper or polymer film preferred for use as packaging systems may be designed in a very wide variety of ways, for example as inflated pouches without a center seam or as pouches with a center seam which are sealed by heat (high-temperature melting), adhesives, or adhesive tapes. Single-layer pouch and bag materials are the known papers, which may optionally be impregnated, and also polymer films, which may optionally be coextruded. Polymer films that can be used as a packaging system in the context of the present invention are specified, for example, in Hans Dominghaus "*Die Kunststoffe und ihre Eigenschaften*", 3$^{rd}$ Edition, VDI Verlag, Düsseldorf, 1988, page 193. Figure 111 shown therein also gives indications of the water vapor permeability of the materials mentioned.

Although it is possible, in addition to said films and papers, to also use wax-coated papers in the form of cardboard packaging as a packaging system for the shaped bodies, it is preferred in the context of the present invention for the packaging system not to comprise any cardboard boxes made of wax-coated paper.

No requirements of any kind are imposed on the optional secondary packaging, meaning that all customary materials and systems can be used here.

Preference is likewise given to embodiments in which the packaging system is of resealable configuration. It has, for example, proven practicable to use, as the packaging system, a resealable small tube made of glass, plastic or metal. In this way it is possible to optimize the dosability of the hair-coloring products, meaning that the consumer can, for example, be instructed to use one shaped body in each case per defined hair length unit. Packaging systems which have a microperforation may also be realized with preference in accordance with the invention.

The present invention secondly provides for the use of the shaped bodies described above for the preparation of a means for coloring keratin fibers.

The present invention thirdly provides a method of coloring keratin fibers in which one or more shaped bodies are dissolved in water, the resulting preparation is applied to the fibers and, after a contact time, rinsed out again.

Although, in principle, it is preferred to incorporate all active ingredients required for the hair coloration except for the solvent into the shaped body, it may nevertheless be preferred according to the invention to add further active ingredients to the preparation obtained by dissolving the tablet in water. For example, the consumer may be instructed to add a special coloring component for further shading, or a further oxidation component for further lightening.

According to the invention, it may also be preferred to add to this preparation, directly prior to application, further active ingredients which cannot be stably formulated in the shaped body, such as, for example, special enzyme preparations or liquid care components.

In this connection, the application temperatures may be in a range between 15 and 40° C., preferably at the temperature of the scalp. The contact time is usually about 5 to 45, in particular 15 to 30, minutes. If no considerable surfactant-containing carrier has been used, it may be preferred to then cleanse the head treated in this way with a shampoo.

EXAMPLES

All amounts given in the examples are in percentages by weight.

The following hair-coloring shaped bodies were prepared:

Example 1

| Phase 1 | |
|---|---|
| 3-methyl-4-aminophenol | 0.1 |
| 2-amino-3-hydroxypyridine | 0.1 |
| Texapon ® K 1296 PLV[1] | 2.0 |
| Avicel ® pH 102[2] | 30.0 |
| Ammonium sulfate | 1.0 |
| Arginine | 10.0 |
| D(+)-lactose | ad 100 |
| Optigel ® SH[3] | 7.5 |
| Amaze ®[4] | 2.5 |
| Jaguar ® HP 120[5] | 7.5 |
| Luviskol ® K30[6] | 2.5 |

[1]Lauryl sulfate, sodium salt (powder; INCI name: sodium lauryl sulfate) (HENKEL)
[2]Microcrystalline cellulose (FMC Corporation)
[3]Synthetic magnesium phyllosilicate (Süd Chemie)
[4]Modified starch (INCI name: Corn Starch modified) (National Starch)
[5]Hydroxypropylguar (INCI name: Hydroxypropyl Guar) (Rhodia)
[6]Polyvinylpyrrolidone (INCI name: PVP) (BASF)

| Phase 2 | |
|---|---|
| D(+)-lactose | 100 |

| Phase 3 | |
|---|---|
| Carbamide perhydrate[7] | 100 |

[7]Urea-hydrogen peroxide (INCI name: Urea Peroxide) (Peroxid Chemie)

1.8 g of the preparation of phase 1 were introduced into a compression cylinder of a tableting machine from Fann Instrument Company and lightly compressed with a punch. 0.2 g of phase 2 were then coated over phase 1 and likewise lightly pressed using a punch. 2.0 g of phase 3 were then coated over the compact and likewise lightly pressed.

Finally, the overall tablet was compressed with a compression force of 13.3KN for 30 sec before being removed from the press. This corresponds, for a tablet diameter of 2.9 cm, to a pressure of 2013N/cm$^2$ of tablet surface. The tablet has a density of 0.86 g/cm$^3$.

Dyeing:

The tablet prepared in this way was dissolved with stirring (with a glass rod) at room temperature in 20 ml of water over the course of 2 minutes to form a color gel. Without stirring, 4 minutes were required to dissolve the tablet completely. The resulting gel was applied to 5 cm-long strands of standardized, 80% gray, but not particularly pretreated human hair (Kerling). After a contact time of 30 min at 32° C., the hair was rinsed, washed with a commercial hair cleanser and then dried. The fibers had a mid-blond coloration.

Example 2

| Phase 1 | |
| --- | --- |
| p-Tolylenediamine sulfate | 3.2 |
| 4-Chlororesorcinol | 1.4 |
| Resorcinol | 0.8 |
| 4-Amino-3-methylphenol | 0.6 |
| 5-Amino-2-methylphenol | 0.5 |
| Texapon ® K 1296 PLV | 2.0 |
| Avicel ® pH 102 | 30.0 |
| Ammonium sulfate | 1.0 |
| Arginine | 10.0 |
| D(+)-Lactose | ad 100 |
| Optigel ® SH | 15.0 |
| Amaze ® | 5.0 |
| Jaguar ® HP 120 | 15.0 |
| Luviskol ® K30 | 5.0 |

A tablet was compressed analogously to the preparation procedure of Example 1, and corresponding strands were colored using the resulting coloring gel. The strands had a hazelnut-brown coloration.

Example 3

| Phase 1 | |
| --- | --- |
| p-Tolylenediamine sulfate | 1.1 |
| 4-Chlororesorcinol | 1.0 |
| 4-Amino-3-methylphenol | 0.7 |
| m-Aminophenol | 0.2 |
| Texapon ® K 1296 PLV | 2.0 |
| Avicel ® pH 102 | 30.0 |
| Ammonium sulfate | 1.0 |
| Arginine | 10.0 |
| D(+)-Lactose | ad 100 |
| Optigel ® SH | 15.0 |
| Amaze ® | 5.0 |
| Jaguar ® HP 120 | 15.0 |
| Luviskol ® K30 | 5.0 |

A tablet was compressed analogously to the preparation procedure of Example 1, and corresponding strands were colored using the resulting coloring gel. The strands had a mid-blond coloration.

Example 4

| Phase 1 | |
| --- | --- |
| p-Tolylenediamine sulfate | 1.6 |
| 1-(β-Hydroxyethyl)amino-4-methyl-2-nitrobenzene | 0.7 |
| 4-chlororesorcinol | 0.5 |
| 4-Amino-3-methylphenol | 5.4 |
| 2,7-Dihydroxynaphthaline | 1.1 |
| 5-Amino-2-methylphenol | 5.1 |

| -continued | |
| --- | --- |
| Phase 1 | |
| Texapon ® K 1296 PLV | 2.0 |
| Avicel ® pH 102 | 30.0 |
| Ammonium sulfate | 1.0 |
| Arginine | 10.0 |
| D(+)-Lactose | ad 100 |
| Optigel ® SH | 15.0 |
| Amaze ® | 5.0 |
| Jaguar ® HP 120 | 15.0 |
| Luviskol ® K30 | 5.0 |

A tablet was compressed analogously to the preparation procedure of Example 1 and corresponding strands were colored using the resulting coloring gel. The strands had an intensive red coloration.

What is claimed is:

1. A shaped body for coloring keratin fibers comprising, in a cosmetically acceptable carrier:

a) at least one dye precursor;

b) at least one oxidizing agent;

c) at least one alkalinizing agent, and d) a dissolution accelerator, wherein said dissolution accelerator consists of gas evolving components, a preformed or enclosed gas, a disintegrant, or mixtures thereof, and wherein said gas evolving components, when present, are present in an amount of at least 10%, by weight, and said disintegrants, when present, are present in an amount of from 0.5 to 50%, by weight.

2. The shaped body of claim 1, wherein the alkalinizing agent is a solid.

3. The shaped body of claim 2, wherein the alkalinizing agent comprises an amino acid or an oligopeptide having at least one amino group and a carboxyl or a sulfo group, wherein the amino acid or oligopeptide has a pH of 9 or greater in water at a concentration of 2.5 percent by weight, based on the total weight of the water and the amino acid or oligopeptide.

4. The shaped body of claim 3, wherein the alkalinizing agent comprises an α-amino acid.

5. The shaped body of claim 4, wherein the alkalinizing agent comprises arginine.

6. The shaped body of claim 1 wherein the dye precursor comprises at least one developer component.

7. The shaped body of claim 1 wherein the dye precursor comprises at least one indole derivative or indoline derivative, or combinations thereof.

8. The shaped body of claim 1, wherein the oxidizing agent comprises at least one addition product of hydrogen peroxide.

9. The shaped body of claim 8, wherein the oxidizing agent comprises a percarbamide.

10. The shaped body of claim 1, wherein the dissolution accelerator comprises a disintegration auxiliary.

11. The shaped body of claim 1 wherein the shaped body comprises at least three layers, wherein a first layer (A) comprises the dye precursor and the alkalinizing agent, wherein a second layer (B) comprises an inert interlayer and wherein a third layer (C) comprises the oxidizing agent.

12. The shaped body of claim 11, wherein the layers have a stack-like structure such that the layer (B) is disposed in between and separates the layer (A) and the layer (C).

13. The shaped body of claim 11, wherein the layer (A) is completely covered by the layer (B), and the layer (B) is completely covered by the layer (C).

14. The shaped body as claimed in claim 11, wherein the layer (C) is completely covered by the layer (B), and the layer (B) is completely covered by the layer (A).

15. The shaped body of claim 11, wherein the alkalinizing agent comprises an amino acid or an oligopeptide having at least one amino group and a carboxyl or a sulfo group, wherein the amino acid or oligopeptide has a pH of 9 or greater in water at a concentration of 2.5 percent by weight, based on the total weight of the water and the amino acid or oligopeptide.

16. The shaped body of claim 1 wherein the shaped body is formed at least in part by compressing one or more individual constituents present in the shaped body, and wherein at least one of the individual constituents or the overall shaped body, or both is coated with a coating.

17. The shaped body of claim 1, wherein the shaped body, upon dissolution in a composition comprising water, forms a gel.

18. The shaped body of claim 1, wherein the shaped body is covered by a primary packaging.

19. A method of coloring keratin fibers comprising:
  i) disintegrating or dissolving or both at least one shaped body of claim 1 in a composition comprising water to form a coloring composition;
  ii) applying the coloring composition to keratin fibers for a contact time; and
  iii) rinsing the keratin fibers after the contact time.

20. The method of claim 19, wherein the alkalinizing agent comprises an amino acid or an oligopeptide having at least one amino group and a carboxyl or a sulfo group, wherein the amino acid or oligopeptide has a pH of 9 or greater in water at a concentration of 2.5 percent by weight, based on the total weight of the water and the amino acid or oligopeptide.

21. The method of claim 19 wherein the shaped body comprises at least three layers, wherein a first layer (A) comprises the dye precursor and the alkalinizing agent, wherein a second layer (B) comprises an inert interlayer and wherein a third layer (C) comprises the oxidizing agent.

* * * * *

UNITED STATES PATENT AND TRADEMARK OFFICE
CERTIFICATE OF CORRECTION

PATENT NO. : 6,790,240 B2
DATED : September 14, 2004
INVENTOR(S) : Schulze zur Wiesche et al.

It is certified that error appears in the above-identified patent and that said Letters Patent is hereby corrected as shown below:

Title page,
Item [73], Assignee, "aug" should read -- auf --.

Signed and Sealed this

Fifteenth Day of February, 2005

JON W. DUDAS
*Director of the United States Patent and Trademark Office*